United States Patent [19]

McCoy et al.

[11] Patent Number: 5,358,963
[45] Date of Patent: Oct. 25, 1994

[54] SYNERGISTIC ANTIMICROBIAL COMPOSITIONS CONTAINING 2-(2-BROMO-2-NITROETHENYL) FURAN

[75] Inventors: William F. McCoy; Geoffrey A. Brown, both of W. Lafayette, Ind.

[73] Assignee: Great Lakes Chemical Corporation, W. Lafayette, Ind.

[21] Appl. No.: 75,824

[22] Filed: Jun. 11, 1993

Related U.S. Application Data

[62] Division of Ser. No. 918,973, Jul. 24, 1992, Pat. No. 5,246,963.

[51] Int. Cl.$^5$ .................. A01N 37/34; A01N 43/08
[52] U.S. Cl. .................. 514/471; 514/527
[58] Field of Search .................. 514/471, 527

[56] References Cited

U.S. PATENT DOCUMENTS

| | | | |
|---|---|---|---|
| 2,335,384 | 11/1943 | Bousquet | 167/22 |
| 3,833,731 | 9/1974 | Grier et al. | 424/304 |
| 4,604,405 | 8/1986 | Jakubowski | 514/326 |
| 4,612,328 | 9/1986 | Jakubowski | 514/515 |
| 4,655,815 | 4/1987 | Jakubowski | 71/67 |
| 4,661,518 | 4/1987 | LaMarre et al. | 514/528 |
| 4,916,158 | 4/1990 | Whitekettle et al. | 514/515 |
| 4,916,164 | 4/1990 | Whitekettle | 514/665 |
| 4,965,377 | 10/1990 | McCoy et al. | 549/491 |
| 5,030,659 | 7/1991 | Bansemir et al. | 514/613 |
| 5,034,405 | 7/1991 | Jakubowski | 514/369 |
| 5,063,217 | 11/1991 | Whitekettle et al. | 514/75 |
| 5,124,355 | 6/1992 | Tully et al. | 514/526 |

OTHER PUBLICATIONS

Kull et al., "Mixtures of Quaternary Ammonium Compounds and Long-Chain Fatty Acids as Antifungal Agents," *Applied Microbiology* 9:538–41 (1961).

*Primary Examiner*—Allen J. Robinson
*Attorney, Agent, or Firm*—Woodard, Emhardt, Naughton Moriarty & McNett

[57] ABSTRACT

Synergistic compositions for inhibiting microbial growth contain synergistic mixtures including 2-(2-bromo-2-nitroethenyl)furan ("BNEF") and a compound selected from the group consisting of beta-nitrostyrene ("NS"), beta-bromo-beta-nitrostyrene ("BNS"), methylchloro/isothiazolone ("IZN"), methylenebisthiocyanate ("MBT"), 2,2-dibromo-3-nitrilopropionamide ("DBNPA"), 2-bromo-2-bromomethyl-glutaronitrile ("BBMGN"), alkyldimethylbenzylammonium chloride ("ADBAC"), and beta-nitrovinyl furan ("NVF"). The synergistic compositions are effective against a wide spectrum of bacteria, algae and fungi. An antimicrobial composition comprising the synergistic mixture and a carrier is also disclosed.

3 Claims, No Drawings

SYNERGISTIC ANTIMICROBIAL COMPOSITIONS CONTAINING 2-(2-BROMO-2-NITROETHENYL) FURAN

This application is a division of co-pending application Ser. No. 07/918,973, filed Jul. 24, 1992, now U.S. Pat. No. 5,246,963.

FIELD OF INVENTION

The present invention relates generally to antimicrobial compositions, and more particularly to new antimicrobial compositions comprising synergistic mixtures of 2-(2-bromo-2-nitroethenyl)furan ("BNEF") and certain other biocides.

BACKGROUND OF THE INVENTION

The use of antimicrobial agents to eliminate or control the growth of various microorganisms is widely known. For example, it is known to use antimicrobial agents to control the growth of microorganisms in a variety of industrial processes, including those relating to the paint, pulp, paper, oil, rubber and tobacco industries; to use antimicrobials in commercial settings, particularly to disinfect contaminated surfaces; and to include antimicrobial agents in a wide variety of household goods such as foods, cosmetics and toiletries.

To accommodate such needs, a variety of antimicrobial agents are known. However, despite the many commercially available antimicrobials, no single agent is entirely suitable for every application. Problems with efficacy, safety, environmental acceptability and cost make certain antimicrobials more or less suitable for a particular application.

Certain advantages of using a combination of antimicrobial agents in a single application are known in the art. For example, it is known that a combination of agents may provide an antimicrobial which is effective against a broader spectrum of microbes than are controlled by a single agent alone. This broad spectrum coverage is especially useful in industrial applications where a diversity of microorganisms is frequently encountered.

It is also known that using a combination of antimicrobials can make the agents more effective when the antimicrobial composition is to be used over an extended course of treatment. One reason for this increased effectiveness is that a combination of antimicrobials is less susceptible to having the targeted microbes develop a resistance to the antimicrobial agent because microorganisms cannot readily adapt to more than one active ingredient at a time.

Moreover, using a combination of agents enables one to take advantage of antimicrobials which have different, yet complementary, physiochemical properties.

In light of this background, there is a continuing need for unique antimicrobial compositions comprising combinations of antimicrobial agents. The present invention addresses this need.

SUMMARY OF THE INVENTION

One preferred embodiment of the present invention provides a synergistic composition for inhibiting microbial growth comprising 2-(2-bromo-2-nitroethenyl)furan ("BNEF") and a compound (i.e. one or more compounds) selected from the group consisting of beta-nitrostyrene ("NS"), beta-bromo-beta-nitrostyrene ("BNS"), methylchloro/isothiazolone ("IZN"), methylenebisthiocyanate ("MBT"), 2,2-dibromo-3-nitrilopropionamide ("DBNPA"), 2-bromo-2-bromomethylglutaronitrile ("BBMGN"), alkyldimethylbenzylammonium chloride ("ADBAC"), and beta-nitrovinyl furan ("NVF"). These synergistic compositions may further include a carrier to provide the antimicrobial agent in liquid form.

Another preferred embodiment of the invention relates to an antimicrobial composition comprising a synergistic mixture including 2-(2-bromo-2-nitroethenyl)furan ("BNEF") and a compound (i.e. one or more compounds) selected from the group consisting of beta-nitrostyrene ("NS"), beta-bromo-beta-nitrostyrene ("BNS"), methylchloro/isothiazolone ("IZN"), methylenebisthiocyanate ("MBT"), 2,2-dibromo-3-nitrilopropionamide ("DBNPA"), 2-bromo-2-bromomethylglutaronitrile ("BBMGN"), alkyldimethylbenzylammonium chloride ("ADBAC"), and beta-nitrovinyl furan ("NVF") and a carrier in liquid form.

Still another preferred embodiment of the invention provides a method of inhibiting growth of microbes. This method comprises contacting the microbes with an antimicrobially effective amount of a synergistic composition including 2-(2-bromo-2-nitroethenyl)furan ("BNEF") and a compound (i.e. one or more compounds) selected from the group consisting of beta-nitrostyrene ("NS"), beta-bromo-beta-nitrostyrene ("BNS"), methylchloro/isothiazolone ("IZN"), methylenebisthiocyanate ("MBT"), 2,2-dibromo-3-nitrilopropionamide ("DBNPA"), 2-bromo-2-bromomethylglutaronitrile ("BBMGN"), alkyldimethylbenzylammonium chloride ("ADBAC"), and beta-nitrovinyl furan ("NVF").

It is one object of the present invention to provide new, synergistic mixtures for use as antimicrobial agents.

Another object of the invention is to provide an antimicrobial composition which comprises the synergistic mixtures in a liquid carrier.

Still another object of the invention is to provide methods for inhibiting microbial growth using the synergistic mixtures.

Related objects and advantages of the present invention will be apparent from the following description.

DESCRIPTION OF THE PREFERRED EMBODIMENT

For the purposes of promoting an understanding of the principles of the invention, reference will now be made to certain embodiments and specific language will be used to describe the same. It will nevertheless be understood that no limitation of the scope of the invention is thereby intended, such alterations and further modifications and applications of the principles of the invention as described herein being contemplated as would normally occur to one skilled in the art to which the invention relates.

The present invention relates to synergistic mixtures of 2-(2-bromo-2-nitroethenyl)furan ("BNEF") and other biocides. The synergistic mixtures are active against Gram negative bacteria such as *Pseudomonas aeruginosa*, Gram positive bacteria such as *Bacillus subtilis*, fungi such as *Aspergillus niger* and *Chaetomium globosum* (molds), and fungi such as *Saccharomyces sp.* (yeasts).

Concerning the specific components of the synergistic compositions, BNEF can be produced from furfural, an inexpensive biodegradable agricultural waste product, and is preferably formed according to the method set forth in U.S. Pat. No. 4,965,377 to McCoy and Thornburgh. The other antimicrobials of the present invention are commercially available and can be made by procedures known to the art.

As indicated, the present invention relates to synergistic combinations of antimicrobial agents. In this regard, as known, synergism refers to a case in which the performance of two or more active ingredients is improved relative to the sum of their individual performances. The method used to determine synergism is generally disclosed by Kull et. al., in "Mixtures of Quaternary Ammonium Compounds and Long-chain Fatty Acids as Antifungal Agents," *Applied Microbiology* 9:538–41 (1961), and is well known in the art.

The Kull et al. method of determining synergism defines a "Synergism Index" as follows:

$$Q_A/Q_a + Q_B/Q_b = \text{Synergism Index (SI)};$$

where $Q_a$ and $Q_b$ are the quantities of compound A or B that produce an endpoint when acting alone, and where $Q_A$ and $Q_B$ are the quantities of compound A or B acting in the A/B mixture required to produce an endpoint. The endpoint is defined by the particular test method employed, as for example the ASTM standardized tests for the Minimum Inhibitory Concentration (MIC).

To determine synergism, one evaluates the Synergism Index. Where SI is equal to 1, the performance of the combination of ingredients is said to be additive. In that case the performance of the ingredients in the mixture is equal to the sum of their individual performances, and no synergism is displayed. Where the synergism index is greater than 1, antagonism exists. In that case, the performance of the ingredients in the mixture is less than the sum of their individual performances and synergism is again not displayed Where the SI is less than 1, the performance of the mixture superior to the sum of the individual performances, and synergism exists.

The synergistic compositions disclosed herein are preferably dissolved or otherwise incorporated in a liquid carrier prior to use but may also be added directly to aqueous systems. Although a wide variety of carriers may be used, preferred carriers include tetrahydrofurfuryl alcohol, dimethyl formamide, N-methylpyrrolidone, and propylene carbonate. When in a liquid carrier, the concentration of active ingredients together may be any concentration and is limited only by the amounts that can be advantageously incorporated in the carrier used. For example, where a composition in solution form is desired, the concentration of actives will of course be limited by the solubility of the actives in the particular carrier employed. In preferred cases, the actives together will comprise up to about 20%, most often about 1–10%, of the liquid composition with the carrier comprising the remainder of the composition.

EXAMPLE 1

A synergistic composition according to the present invention can be made by dissolving BNEF and beta-nitrostyrene ("NS") together in THFA at room temperature. Alternatively, the active ingredients can be added to the media to be treated from separate solutions to achieve the same synergistic effect. A wide range of ratios of the two active ingredients can be used, depending on the microorganism to be controlled. For example, to control the growth of *Pseudomonas aeruginosa*, the ratio of BNEF to NS may be as low as 1:125. To control growth of *Chaetomium globosum*, the ratio of BNEF to NS may be 2:1. Preferred ratios of BNEF to NS for use with other microorganisms typically lie in the range of about 2:1 to about 1:125.

EXAMPLES 2–8

Further synergistic compositions according to the present invention are made by dissolving BNEF and any member of the group consisting of beta-bromo-beta-nitrostyrene ("BNS"), methylchloro/isothiazolone ("IZN"), methylenebisthiocyanate ("MBT"), 2,2-dibromo-3-nitrilopropionamide ("DBNPA"), 2-bromo-2-bromomethyl-glutaronitrile ("BBMGN"), alkyldimethylbenzylammonium chloride ("ADBAC"), and beta-nitrovinyl furan ("NVF") together in THFA at room temperature. Again, a wide range of ratios of the two active ingredients can be used, depending on several factors including the microorganism to be controlled. For example, preferred ratios of BNEF to the other antimicrobials generally are about 8:1 to about 1:32 for BNS; about 7:1 to about 1:1 for IZN; about 3:1 to about 1:1 for MBT; about 1:1 to about 1:2500 for DBNPA; about 1:1 to about 1:15 for BBMGN; about 1:5 to about 1:41 for ADBAC; and about 1:1 to about 1:89 for NVF.

EXPERIMENTAL EVALUATIONS

Tables 1–8 disclose synergistic combinations of BNEF and other biocides. The method used for this study was a minimum inhibitory concentration ("MIC") analysis in an appropriate growth medium. Pure cultures of the microorganisms were obtained from the American Type Culture Collection (ATCC) or directly from the environment and identified by standard biochemical and microscopic tests. Each organism was grown in nutrient-rich media recommended by ATCC. Sterile media was then inoculated with the test organism and a dose of one or both antimicrobials. The minimum inhibitory concentration (MIC) of BNEF and the other biocide was first separately determined. Then, a wide range of BNEF/other biocide combinations were tested systematically until synergistic compositions were discovered. In the experimental evaluations provided herewith, the MIC endpoint for each organism is defined as the lowest concentration which completely inhibits microbial growth for up to 48 hours of incubation for bacteria and 72 hours for fungi. In the following Tables 1–8, data designated as Qa and QA in each case is for BNEF, and data designated as Qb and QB in each case is the other antimicrobial (i.e., NS, BNS, IZN, etc.).

TABLE 1

| BNEF with Beta-nitrostyrene (NS) | | | | | | |
|---|---|---|---|---|---|---|
| | Concentrations (ppm) | | | | | |
| Microorganism | Qa | Qb | QA | QB | SI | QA:QB |
| *Pseudomonas aeruginosa* | 1.56 | 25.0 | 0.78 | 6.25 | 0.75 | 1:8 |
| | | | 0.39 | 12.50 | 0.75 | 1:32 |
| | | | 0.78 | 3.10 | 0.63 | 1:4 |
| | | | 0.20 | 12.50 | 0.63 | 1:62.5 |
| | | | 0.10 | 12.50 | 0.56 | 1:125 |
| *Bacillus subtilis* | 3.10 | 12.50 | 1.56 | 3.13 | 0.75 | 1:2 |
| | | | 0.78 | 6.25 | 0.75 | 1:8 |
| *Aspergillus niger* | 0.78 | 3.00 | 0.20 | 1.50 | 0.75 | 1:7.5 |
| *Chaetomium globosum* | 1.56 | 3.00 | 0.78 | 0.38 | 0.63 | 2:1 |
| | | | 0.39 | 1.50 | 0.75 | 1:4 |
| | | | 0.20 | 1.50 | 0.63 | 1:7.5 |
| *Saccharomyces sp.* | 0.39 | 1.50 | 0.20 | 0.38 | 0.75 | 1:2 |

TABLE 2

BNEF with beta-bromo-beta-nitrostyrene (BNS)

| Microorganism | Qa | Qb | QA | QB | SI | QA:QB |
|---|---|---|---|---|---|---|
| Pseudomonas aeruginosa | 2.08 | 4.25 | 1.04 | 0.13 | 0.53 | 8:1 |
| | | | 1.04 | 0.26 | 0.56 | 4:1 |
| | | | 1.04 | 0.53 | 0.75 | 2:1 |
| | | | 0.52 | 1.10 | 0.50 | 1:2 |
| | | | 0.26 | 2.10 | 0.63 | 1:8 |
| | | | 0.13 | 2.10 | 0.56 | 1:16 |
| Bacillus subtilis | 3.10 | 12.50 | 0.78 | 0.78 | 0.31 | 1:1 |
| | | | 0.78 | 1.56 | 0.37 | 1:2 |
| | | | 0.78 | 3.13 | 0.50 | 1:4 |
| | | | 0.39 | 1.56 | 0.25 | 1:4 |
| | | | 0.39 | 3.13 | 0.38 | 1:8 |
| | | | 0.39 | 6.25 | 0.63 | 1:16 |
| | | | 0.20 | 6.25 | 0.63 | 1:31.3 |
| Aspergillus niger | 0.78 | 3.00 | 0.39 | 0.75 | 0.75 | 1:2 |
| | | | 0.20 | 1.50 | 0.75 | 1:7.5 |
| | | | 0.10 | 1.50 | 0.62 | 1:15 |
| Chaetomium globosum | 1.56 | 3.00 | 0.78 | 0.75 | 0.75 | 1:1 |
| | | | 0.39 | 1.50 | 0.75 | 1:3.8 |
| Saccharomyces sp. | 0.39 | 1.50 | 0.20 | 0.38 | 0.75 | 1:1.9 |
| | | | 0.10 | 0.75 | 0.75 | 1:7.5 |
| | | | 0.05 | 0.75 | 0.63 | 1:15 |

TABLE 3

BNEF with methylchloro/isothiazolone (IZN)

| Microorganism | Qa | Qb | QA | QB | SI | QA:QB |
|---|---|---|---|---|---|---|
| Pseudomonas aeruginosa | 1.56 | 0.43 | 0.78 | 0.27 | 0.56 | 2.8:1 |
| | | | 0.78 | 0.53 | 0.62 | 1.5:1 |
| | | | 0.78 | 0.11 | 0.75 | 7:1 |
| | | | 0.39 | 0.11 | 0.50 | 3.5:1 |
| | | | 0.39 | 0.21 | 0.75 | 2:1 |
| | | | 0.20 | 0.21 | 0.63 | 1:1 |
| Bacillus subtilis | 3.10 | 0.43 | 0.78 | 0.11 | 0.51 | 7:1 |
| | | | 0.39 | 0.21 | 0.63 | 1.8:1 |
| Saccharomyces sp. | 0.39 | 0.80 | 0.20 | 0.10 | 0.63 | 2:1 |
| | | | 0.20 | 0.20 | 0.75 | 1:1 |
| | | | 0.10 | 0.40 | 0.75 | 1:4 |
| | | | 0.05 | 0.40 | 0.63 | 1:8 |

TABLE 4

BNEF with methylenebisthiocyanate (MBT)

| Microorganism | Qa | Qb | QA | QB | SI | QA:QB |
|---|---|---|---|---|---|---|
| Pseudomonas aeruginosa | 2.08 | 0.63 | 1.04 | 0.78 | 0.62 | 1.3:1 |
| | | | 0.52 | 0.16 | 0.50 | 3.3:1 |
| | | | 0.52 | 0.31 | 0.75 | 1.7:1 |
| | | | 0.26 | 0.31 | 0.63 | 1:1.2 |

TABLE 5

BNEF with 2,2-dibromo-3-nitrilopropionamide (DBNPA)

| Microorganism | Qa | Qb | QA | QB | SI | QA:QB |
|---|---|---|---|---|---|---|
| Pseudomonas aeruginosa | 2.08 | 5.20 | 1.04 | 1.30 | 0.75 | 1:1.3 |
| Bacillus subtilis | 0.78 | 3.90 | 0.39 | 0.98 | 0.75 | 1:2.5 |
| Aspergillus niger | 0.78 | 250.00 | 0.20 | 125.00 | 0.75 | 1:625 |
| | | | 0.10 | 125.00 | 0.63 | 1:1250 |
| | | | 0.05 | 125.00 | 0.56 | 1:2500 |

TABLE 6

BNEF with 2-bromo-2-bromomethyl-glutaronitrile (BBMGN)

| Microorganism | Qa | Qb | QA | QB | SI | QA:QB |
|---|---|---|---|---|---|---|
| Pseudomonas aeruginosa | 2.08 | 7.80 | 1.04 | 0.98 | 0.63 | 1.1:1 |
| | | | 1.04 | 1.95 | 0.75 | 1:1.9 |
| | | | 0.52 | 1.95 | 0.50 | 1:3.8 |

TABLE 6-continued

BNEF with 2-bromo-2-bromomethyl-glutaronitrile (BBMGN)

| Microorganism | Qa | Qb | QA | QB | SI | QA:QB |
|---|---|---|---|---|---|---|
| | | | 0.52 | 3.90 | 0.75 | 1:7.5 |
| | | | 0.26 | 3.90 | 0.63 | 1:15 |
| Bacillus subtilis | 0.78 | 3.90 | 0.39 | 0.97 | 0.75 | 1:2.5 |
| | | | 0.20 | 1.94 | 0.75 | 1:9.7 |

TABLE 7

BNEF with alkyldimethylbenzylammonium chloride (ADBAC)

| Microorganism | Qa | Qb | QA | QB | SI | QA:QB |
|---|---|---|---|---|---|---|
| Aspergillus niger | 0.78 | 15.6 | 0.39 | 1.95 | 0.51 | 1:5 |
| | | | 0.39 | 3.90 | 0.75 | 1:10 |
| | | | 0.19 | 7.80 | 0.50 | 1:41 |
| Chaetomium globosum | 1.56 | 7.80 | 0.39 | 3.90 | 0.75 | 1:10 |

TABLE 8

BNEF with beta-nitrovinyl furan (NVF)

| Microorganism | Qa | Qb | QA | QB | SI | QA:QB |
|---|---|---|---|---|---|---|
| Pseudomonas aeruginosa | 2.08 | 12.50 | 1.04 | 1.56 | 0.62 | 1:1.5 |
| | | | 1.04 | 3.13 | 0.75 | 1:3 |
| | | | 0.52 | 3.13 | 0.50 | 1:6 |
| | | | 0.52 | 6.25 | 0.75 | 1:12 |
| | | | 0.26 | 6.25 | 0.63 | 1:24 |
| | | | 0.13 | 6.25 | 0.56 | 1:48 |
| | | | 0.07 | 6.25 | 0.53 | 1:89 |
| Bacillus subtilis | 0.78 | 12.50 | 0.19 | 6.25 | 0.75 | 1:33 |
| | | | 0.10 | 6.25 | 0.51 | 1:62.5 |

The antimicrobial compositions described above can be seen to exhibit synergistic activity with respect to a variety of common microorganisms. However, the examples disclosed herein should not be considered to disclose all possible microorganisms which may be controlled by the synergistic combinations, nor should the identified ranges be viewed as limiting in nature. All synergistic antimicrobial combinations of the identified ingredients are intended to be within the scope of the present invention, and all antimicrobial uses thereof are intended to be claimed.

I claim:

1. A method of inhibiting the growth of *Pseudomonas aeruginosa* comprising contacting said *Pseudomonas aeruginosa* with an effective amount of a synergistic composition including
   2-(2-bromo-2-nitroethenyl)furan and
   2,2-dibromo-3-nitrilopropionamide, the weight ratio of
   2-(2-bromo-2-nitroethenyl)furan to
   2-2-dibromo-3-nitrilopropionamide being about 1:1.3.

2. A method of inhibiting the growth of *Bacillus subtilis* comprising contacting said *Bacillus subtilis* with an effective amount of a synergistic composition including
   2-(2-bromo-2-nitroethenyl)furan and
   2,2-dibromo-3-nitrilopropionamide, the weight ratio of
   2-(2-bromo-2-nitroethenyl)furan to
   2,2-dibromo-3-nitrilopropionamide being about 1:25.

3. A method of inhibiting the growth of *Aspergillus niger* comprising contacting said *Aspergillus niger* with an effective amount of a synergistic composition including
   2-(2-bromo-2-nitroethenyl)furan and
   2,2-dibromo-3-nitrilopropionamide, the weight ratio of
   2-(2-bromo-2-nitroethenyl)furan to
   2,2-dibromo-3-nitrilopropionamide being from about 1:625 to about 1:2500.

* * * * *